(12) United States Patent
Tomita et al.

(10) Patent No.: US 6,214,591 B1
(45) Date of Patent: Apr. 10, 2001

(54) METHODS FOR PRODUCING L-VALINE AND L-LEUCINE

(75) Inventors: Fusao Tomita; Atsushi Yokota, both of Sapporo; Kenichi Hashiguchi, Kawasaki; Masako Ishigooka, Kawasaki; Osamu Kurahashi, Kawasaki, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/231,061

(22) Filed: Jan. 14, 1999

Related U.S. Application Data

(62) Division of application No. 08/793,441, filed as application No. PCT/JP95/01719 on Aug. 30, 1995, now Pat. No. 5,888,783.

(30) Foreign Application Priority Data

Aug. 30, 1994 (JP) .................................... 6/204856

(51) Int. Cl.$^7$ ............................ C12P 13/06; C12P 13/08; C12N 1/20; C12N 1/21
(52) U.S. Cl. .................... 435/115; 435/116; 435/252.33; 435/252.8; 435/320.1
(58) Field of Search ................................ 435/115, 116, 435/252.33, 252.8, 320.1

(56) References Cited

U.S. PATENT DOCUMENTS 5,888,783 * 3/1999 Tomita et al. ........................ 435/115

FOREIGN PATENT DOCUMENTS

| 519113 | 12/1992 | (EP) . |
| 61-185195 | 8/1986 | (JP) . |
| 4-330275 | 11/1992 | (JP) . |
| 5-137568 | 6/1993 | (JP) . |
| WO 8702984 | 5/1987 | (WO) . |

OTHER PUBLICATIONS

A. Herbert et al, "Lipoic Acid Content of *Escherichia coli* and Other Microorganisms", Arch. Microbiol., vol. 106, pp. 259–266, 1975.

A. Yokota et al, "Pyruvic Acid Production by an $F_1$–ATPase–defective Mutant of *Escherichia coli* W1485lip2", Biosci. Biotech. Biochem., vol. 58(12), pp. 2164–2167, 1994.

H. Aida et al, "Amino Acid Fermentation", Gakkai Shuppan Center, pp. 397–422, May 30, 1986.

A. Yokota et al, "Pyruvic acid production by a lipoic acid auxotoph of *Escherichia coli* W1485", Appl. Microbiol Biotechnol., vol. 41, pp. 638–643, 1994.

Derwent Abstract 93–093644 JP05137568 AJINOMOTO KK Jun. 1, 1993.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

L-valine is produced by culturing a microorganism belonging to the genus Escherichia with the capability of producing L-valine or L-leucine wherein it requires lipoic acid for growth, a microorganism belonging to the genus Escherichia with the capability of producing L-valine or L-leucine wherein it is deficient in $H^+$-ATPase activity, a microorganism belonging to the genus Escherichia wit the capability of producing L-valine or L-leucine wherein it requires lipoic acid for growth and is deficient in $H^+$-ATPase activity, in the liquid medium to allow the L-valine to be produced and accumulated in a culture medium, and collecting it.

6 Claims, 5 Drawing Sheets pMWD5 13kb

H : HindIII
P : PstI
B : BamHI
A : AccIII
Bg : BgII
S : SnABI
N : NotI
X : XbaI
& : Impossible to re-cleave SnaBI
AccIII
partial
Self-ligation pMWdAR6 11.7kb

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2841 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: ESCHERICHIA COLI
         (B) STRAIN: MI162

(ix) FEATURE:
         (A) NAME/KEY: CDS
         (B) LOCATION: 957..1055
         (D) OTHER INFORMATION: /note= "IDENTIFICATION METHOD: S"

(ix) FEATURE:
         (A) NAME/KEY: attenuator
         (B) LOCATION: 1081..1104
         (D) OTHER INFORMATION: /note= "IDENTIFICATION METHOD: S"

(ix) FEATURE:
         (A) NAME/KEY: CDS
         (B) LOCATION: 1195..2841
         (D) OTHER INFORMATION: /note= "IDENTIFICATION METHOD: S"

(ix) FEATURE:
         (A) NAME/KEY: misc_feature
         (B) LOCATION: 52..57
         (D) OTHER INFORMATION: /note= "CLEAVAGE SITE: SmaI,
             IDENTIFICATION METHOD: S"

(ix) FEATURE:
         (A) NAME/KEY: misc_feature
         (B) LOCATION: 2395..2400
         (D) OTHER INFORMATION: /note= "CLEAVAGE SITE: KpnI,
             IDENTIFICATION METHOD: S"

(xi) SEQUENCE DESCRIPTION: SEQ ID NO:1:

```
CTCGCTTTCC TTGTTCCTGA CCGATAACAT CACTGAGATC ATGTTGTAGC GCCCGGGATA      60

CTGCATCAGT TGGTTTCGGG CGTTCGAGAG CGTGCTTACC TTCCAGAAAC GCACAGACAG     120

CTTGCAGATG ATCGGCTATC AGGCATCCTT CACCGTTAAT TAGCCCCACT TCATCTTCGT     180

TATCTTTCGC GACGATAATT TTTCTGCCCG ACTTAATAGC TTCAGTTGCA CTGGAGATTG     240

CGCCGGGAAC GCCACGCAGA GCGCCTGTAA GCGCCAGTTC TCCGACTAAT TCATATTCAT     300

CTAACTTATT GGCTGTAAGC TGTTCTGAGG CCGCCAGCAA CGCAATGGCG ATAGGTAAAT     360

CATATCGTCC CCCTTCTTTT GGCAGATCAG CTGGAGCCAG GTTGATGGTG ATTTTTTTCG     420

CCGGATATTC ATATCCGCTA TTGATAATGG CGCTGCGCAC GCGATCGCGA GCTTCTTTTA     480

CCGTTGTTTC TGGTAAGCCC ACCATCGTTA AGCCGGGTAG ACCTTTACTG ATATGTACCT     540

CAACAGTGAT CGGGGGCGCA TTTACTCCCA GGGCTGCGCG GGTATGAACA ATTGACAGTG     600

ACATAAGCCC TCCTTGAGTC ACCATTATGT GCATAAGATA TCGCTGCTGT AGCCCGCTAA     660

TTCGTGAATT TTAGTGGCTG ATTCCTGTTT ATTTGTGCAA GTGAAGTTGA GTTGTTCTGG     720

CGGTGGAATG ATGCTCGCAA AAATGCAGCG GACAAAGGAT GAACTACGAG GAAGGGAACA     780

ACATTCATAC TGAAATTGAA TTTTTTTCAC TCACTATTTT ATTTTTAAAA AACAACAATT     840

TATATTGAAA TTATTAAACG CATCATAAAA ATCGGCCAAA AAATATCTTG TACTATTTAC     900

AAAACCTATG GTAACTCTTT AGGCATTCCT TCGAACAAGA TGCAAGAAAA GACAAA        956
```

```
ATG ACA GCC CTT CTA CGA GTG ATT AGC CTG GTC GTG ATT AGC GTG GTG    1004
Met Thr Ala Leu Leu Arg Val Ile Ser Leu Val Val Ile Ser Val Val
  1               5                  10                  15

GTG ATT ATT ATC CCA CCG TGC GGG GCT GCA CTT GGA CGA GGA AAG GCT    1052
Val Ile Ile Ile Pro Pro Cys Gly Ala Ala Leu Gly Arg Gly Lys Ala
             20                  25                  30

TAG AGATCAAGCC TTAACGAACT AAGACCCCCG CACCGAAAGG TCCGGGGGTT          1105
 *

TTTTTTGACC TTAAAAACAT AACCGAGGAG CAGACAATGA ATAACAGCAC AAAATTCTGT   1165
```

```
TTCTCAAGAT TCAGGACGGG GAACTAACT ATG AAT GGC GCA CAG TGG GTG GTA        1218
                                Met Asn Gly Ala Gln Trp Val Val
                                 1               5

CAT GCG TTG CGG GCA CAG GGT GTG AAC ACC GTT TTC GGT TAT CCG GGT        1266
His Ala Leu Arg Ala Gln Gly Val Asn Thr Val Phe Gly Tyr Pro Gly
         10              15                  20

GGC GCA ATT ATG CCG GTT TAC GAT GCA TTG TAT GAC GGC GGC GTG GAG        1314
Gly Ala Ile Met Pro Val Tyr Asp Ala Leu Tyr Asp Gly Gly Val Glu
 25              30                  35                      40

CAC TTG CTA TGC CGA CAT GAG CAG GGT GCG GCA ATG GCG GCT ATC GGT        1362
His Leu Leu Cys Arg His Glu Gln Gly Ala Ala Met Ala Ala Ile Gly
                 45                  50                  55

TAT GCT CGT GCT ACC GGC AAA ACT GGC GTA TGT ATC GCC ACG TCT GGT        1410
Tyr Ala Arg Ala Thr Gly Lys Thr Gly Val Cys Ile Ala Thr Ser Gly
             60                  65                  70

CCG GGC GCA ACC AAC CTG ATA ACC GGG CTT GCG GAC GCA CTG TTA GAT        1458
Pro Gly Ala Thr Asn Leu Ile Thr Gly Leu Ala Asp Ala Leu Leu Asp
         75                  80                  85

TCC ATC CCT GTT GTT GCC ATC ACC GGT CAA GTG TCC GCA CCG TTT ATC        1506
Ser Ile Pro Val Val Ala Ile Thr Gly Gln Val Ser Ala Pro Phe Ile
     90                  95                 100

GGC ACT GAC GCA TTT CAG GAA GTG GAT GTC CTG GGA TTG TCG TTA GCC        1554
Gly Thr Asp Ala Phe Gln Glu Val Asp Val Leu Gly Leu Ser Leu Ala
105             110                 115                 120

TGT ACC AAG CAT AGC TTT CTG GTG CAG TCG CTG GAA GAG TTG CCG CGC        1602
Cys Thr Lys His Ser Phe Leu Val Gln Ser Leu Glu Glu Leu Pro Arg
                125                 130                 135

ATC ATG GCT GAA GCA TTC GAC GTT GCC TGC TCA GGT CGT CCT GGT CCG        1650
Ile Met Ala Glu Ala Phe Asp Val Ala Cys Ser Gly Arg Pro Gly Pro
            140                 145                 150

GTT CTG GTC GAT ATC CCA AAA GAT ATC CAG TTA GCC AGC GGT GAC CTG        1698
Val Leu Val Asp Ile Pro Lys Asp Ile Gln Leu Ala Ser Gly Asp Leu
                155                 160                 165

GAA CCG TGG TTC ACC ACC GTT GAA AAC GAA GTG ACT TTC CCA CAT GCC        1746
Glu Pro Trp Phe Thr Thr Val Glu Asn Glu Val Thr Phe Pro His Ala
        170                 175                 180

GAA GTT GAG CAA GCG CGC CAG ATG CTG GCA AAA GCG CAA AAA CCG ATG        1794
Glu Val Glu Gln Ala Arg Gln Met Leu Ala Lys Ala Gln Lys Pro Met
185             190                 195                 200

CTG TAC GTT GGC GGT GGC GTG GGT ATG GCG CAG GCA GTT CCG GCT TTG        1842
Leu Tyr Val Gly Gly Gly Val Gly Met Ala Gln Ala Val Pro Ala Leu
                205                 210                 215

CGT GAA TTT CTC GCT GCC ACA AAA ATG CCT GCC ACC TGT ACG CTG AAA        1890
Arg Glu Phe Leu Ala Ala Thr Lys Met Pro Ala Thr Cys Thr Leu Lys
            220                 225                 230

GGG CTG GGC GCA GTA GAA GCA GAT TAT CCG TAC TAT CTG GGC ATG CTG        1938
Gly Leu Gly Ala Val Glu Ala Asp Tyr Pro Tyr Tyr Leu Gly Met Leu
                235                 240                 245

GGG ATG CAC GGC ACC AAA GCG GCA AAC TTC GCG GTG CAG GAG TGT GAC        1986
Gly Met His Gly Thr Lys Ala Ala Asn Phe Ala Val Gln Glu Cys Asp
        250                 255                 260

CTG CTG ATC GCC GTG GGC GCA CGT TTT GAT GAC CGG GTG ACC GGC AAA        2034
Leu Leu Ile Ala Val Gly Ala Arg Phe Asp Asp Arg Val Thr Gly Lys
265             270                 275                 280

CTG AAC ACC TTC GCG CCA CAC GCC AGT GTT ATC CAT ATG GAT ATC GAC        2082
Leu Asn Thr Phe Ala Pro His Ala Ser Val Ile His Met Asp Ile Asp
                285                 290                 295

CCG GCA GAA ATG AAC AAG CTG CGT CAG GCA CAT GTG GCA TTA CAA GGT        2130
Pro Ala Glu Met Asn Lys Leu Arg Gln Ala His Val Ala Leu Gln Gly
```

```
                    300                 305                 310
GAT TTA AAT GCT CTG TTA CCA GCA TTA CAG CAG CCG TTA AAT CAA TGT         2178
Asp Leu Asn Ala Leu Leu Pro Ala Leu Gln Gln Pro Leu Asn Gln Cys
            315                 320                 325

GAC TGG CAG CAA CAC TGC GCG CAG CTG CGT GAT GAA CAT TCC TGG CGT         2226
Asp Trp Gln Gln His Cys Ala Gln Leu Arg Asp Glu His Ser Trp Arg
    330                 335                 340

TAC GAC CAT CCC GGT GAC GCT ATC TAC GCG CCG TTG TTG TTA AAA CAA         2274
Tyr Asp His Pro Gly Asp Ala Ile Tyr Ala Pro Leu Leu Leu Lys Gln
345                 350                 355                 360

CTG TCG GAT CGT AAA CCT GCG GAT TGC GTC GTG ACC ACA GAT GTG GGG         2322
Leu Ser Asp Arg Lys Pro Ala Asp Cys Val Val Thr Thr Asp Val Gly
                365                 370                 375

CAG CAC CAG ATG TGG GCT GCG CAG CAC ATC GCC CAC ACT CGC CCG GAA         2370
Gln His Gln Met Trp Ala Ala Gln His Ile Ala His Thr Arg Pro Glu
            380                 385                 390

AAT TTC ATC ACC TCC AGC GGT TTA GGT ACC ATG GGT TTT GGT TTA CCG         2418
Asn Phe Ile Thr Ser Ser Gly Leu Gly Thr Met Gly Phe Gly Leu Pro
        395                 400                 405

GCG GCG GTT GGC GCA CAA GTC GCG CGA CCG AAC GAT ACC GTT GTC TGT         2466
Ala Ala Val Gly Ala Gln Val Ala Arg Pro Asn Asp Thr Val Val Cys
    410                 415                 420

ATC TCC GGT GAC GGC TCT TTC ATG ATG AAT GTG CAA GAG CTG GGC ACC         2514
Ile Ser Gly Asp Gly Ser Phe Met Met Asn Val Gln Glu Leu Gly Thr
425                 430                 435                 440

GTA AAA CGC AAG CAG TTA CCG TTG AAA ATC GTC TTA CTC GAT AAC CAA         2562
Val Lys Arg Lys Gln Leu Pro Leu Lys Ile Val Leu Leu Asp Asn Gln
                445                 450                 455

CGG TTA GGG ATG GTT CGA CAA TGG CAG CAA CTG TTT TTT CAG GAA CGA         2610
Arg Leu Gly Met Val Arg Gln Trp Gln Gln Leu Phe Phe Gln Glu Arg
            460                 465                 470

TAC AGC GAA ACC ACC CTT ACT GAT AAC CCC GAT TTC CTC ATG TTA GCC         2658
Tyr Ser Glu Thr Thr Leu Thr Asp Asn Pro Asp Phe Leu Met Leu Ala
        475                 480                 485

AGC GCC TTC GGC ATC CAT GGC CAA CAC ATC ACC CGG AAA GAC CAG GTT         2706
Ser Ala Phe Gly Ile His Gly Gln His Ile Thr Arg Lys Asp Gln Val
    490                 495                 500

GAA GCG GCA CTC GAC ACC ATG CTG AAC AGT GAT GGG CCA TAC CTG CTT         2754
Glu Ala Ala Leu Asp Thr Met Leu Asn Ser Asp Gly Pro Tyr Leu Leu
505                 510                 515                 520

CAT GTC TCA ATC GAC GAA CTT GAG AAC GTC TGG CCG CTG GTG CCG CCT         2802
His Val Ser Ile Asp Glu Leu Glu Asn Val Trp Pro Leu Val Pro Pro
                525                 530                 535

GGC GCC AGT AAT TCA GAA ATG TTG GAG AAA TTA TCA TGA                     2841
Gly Ala Ser Asn Ser Glu Met Leu Glu Lys Leu Ser  *
            540                 545
```

(2) INFORMATION FOR SEQ ID NO:2:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30
```

```
Ala Leu Tyr Asp Gly Gly Val Glu His Leu Leu Cys Arg His Glu Gln
         35                  40                  45

Gly Ala Ala Met Ala Ala Ile Gly Tyr Ala Arg Ala Thr Gly Lys Thr
     50                  55                  60

Gly Val Cys Ile Ala Thr Ser Gly Pro Gly Ala Thr Asn Leu Ile Thr
 65                  70                  75                  80

Gly Leu Ala Asp Ala Leu Leu Asp Ser Ile Pro Val Val Ala Ile Thr
                 85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Ala Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
    290                 295                 300

Gln Ala His Val Ala Leu Gln Gly Asp Leu Asn Ala Leu Leu Pro Ala
305                 310                 315                 320

Leu Gln Gln Pro Leu Asn Gln Cys Asp Trp Gln Gln His Cys Ala Gln
                325                 330                 335

Leu Arg Asp Glu His Ser Trp Arg Tyr Asp His Pro Gly Asp Ala Ile
            340                 345                 350

Tyr Ala Pro Leu Leu Leu Lys Gln Leu Ser Asp Arg Lys Pro Ala Asp
        355                 360                 365

Cys Val Val Thr Thr Asp Val Gly Gln His Gln Met Trp Ala Ala Gln
370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
        435                 440                 445
```

```
Lys Ile Val Leu Leu Asp Asn Gln Arg Leu Gly Met Val Arg Gln Trp
    450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile His Gly Gln
                485                 490                 495

His Ile Thr Arg Lys Asp Gln Val Glu Ala Ala Leu Asp Thr Met Leu
                500                 505                 510

Asn Ser Asp Gly Pro Tyr Leu Leu His Val Ser Ile Asp Glu Leu Glu
            515                 520                 525

Asn Val Trp Pro Leu Val Pro Pro Gly Ala Ser Asn Ser Glu Met Leu
    530                 535                 540

Glu Lys Leu Ser
545
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(iii) HYPOTHETICAL: NO (iv) ANTI-SENSE: NO (xi) SEQUENCE DESCRIPTION: SEQ ID NO:3:

TAACATCACT GAGATCATGT TG                                            22

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(iii) HYPOTHETICAL: NO (iv) ANTI-SENSE: NO (xi) SEQUENCE DESCRIPTION: SEQ ID NO:4:

TCTTTTCTTG CATCTTGTTC G                                             21

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(iii) HYPOTHETICAL: NO (iv) ANTI-SENSE: NO (xi) SEQUENCE DESCRIPTION: SEQ ID NO:5:

```
                                      -continued

TCTGTTTCTC AAGATTCAGG AC                                                  22

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(iii) HYPOTHETICAL: NO (iv) ANTI-SENSE: NO (xi) SEQUENCE DESCRIPTION: SEQ ID NO:6:

CGCCGGTAAA CCAAAACCC                                                      19
```

METHODS FOR PRODUCING L-VALINE AND L-LEUCINE

This application is a Divisional of application Ser. No. 08/793,441 filed on Feb. 28, 1997, now U.S. Pat. No. 5,888,783, which was filed as International Application No. PCT/JP95/01719, filed on Aug. 30, 1995.

TECHNICAL FIELD

This invention relates to a microorganism belonging to the genus Escherichia having the capability of producing L-valine or L-leucine and, more particularly, a microorganism whose capability of producing L-valine or L-leucine is enhanced.

BACKGROUND ART

In the past, L-valine and L-leucine have been produced by a method of fermentation primarily using a microorganism belonging to the genus Brevibacterium, Corynebacterium or Serratia or a mutant thereof which produces L-valine or L-leucine (Amino acid fermentation, JAPAN SCIENTIFIC SOCIETY'S PRESS, pp.397–422, 1986). Although the conventional methods have considerably enhanced the productivity of these amino acids, the development of a more efficient, cost-effective technique is required in order to meet increasing demand for L-valine and L-leucine in the future.

On the other hand, a microorganism belonging to the genus Escherichia is potentially utilized as a potent L-valine or L-leucine-producing microorganism due to its rapid growth rate, progress in genetic analysis and plentiful genetic materials. However, there are few reports documenting the production of these amino acids with from Escherichia microorganisms, and as for L-branched chain amino acids, only a few reports deal with the production of L-isoleucine (Japanese Patent Application Laid-Open No. 5-304969(1993) and Japanese Patent Application Laid-Open No. 5-130882(1993).

DISCLOSURE OF THE INVENTION

The object of the present invention, in view of the aforementioned points, is to provide an efficient and cost-effective method for producing L-valine and L-leucine by enhancing the capability of producing L-valine or L-leucine of a microorganism belonging to the genus Escherichia.

As a result of a wholeheartedly conducted study of the production of L-valine and L-leucine by mutants of microorganisms belonging to the genus Escherichia, the present inventors have found that a mutation, whereby lipoic acid is required for growth and/or $H^+$-ATPase is deficient, enhances the capability of producing L-valine or L-leucine of a L-valine or L-leucine-producing microorganism.

Thus, a first microorganism of the present invention is a microorganism belonging to the genus Escherichia and having the capability of producing L-valine or L-leucine, which requires lipoic acid for growth. A second microorganism of the present invention is a microorganism belonging to the genus Escherichia and having the capability of producing L-valine or L-leucine, which is deficient in $H^+$-ATPase. Furthermore, a third microorganism of the present invention is a microorganism belonging to the genus Escherichia and having the capability of producing L-valine or L-leucine, which requires lipoic acid for growth and is deficient in $H^+$-ATPase.

The present invention also provides a method for producing L-valine or L-leucine comprising culturing the aforementioned microorganism in a liquid medium to allow the L-valine or L-leucine to be produced and accumulated in the medium and collecting it.

In the specification, the phrase "$H^+$-ATPase deficient" means that cells do not substantially express $H^+$-ATPase activity, and includes both of that an $H^+$-ATPase gene does not express due to entire or partial deletion of an atp operon coding for eight subunits of $H^+$-ATPase or split of the atp operon and that the $H^+$-ATPase gene has substitution, insertion or deletion of one or more nucleotides therein so that the $H^+$-ATPase protein which is produced by expression of the gene does not have $H^+$-ATPase activity. The ilvGMEDA operon means a operon including each of ilvG, ilvM, ilvE and ilvD genes, and the operon may additionally include ilvA gene, which expresses inactivated threonine deaminase, or may not include ilvA gene substantially.

The invention will be described in detail as follows:

<1> Microorganism of the Present Invention

A microorganism of the invention is one which belongs to the genus Escherichia and has the capability of producing L-valine or L-leucine and has any one of the following properties:

1. Lipoic acid is required for growth.
2. $H^+$-ATPase is deficient.
3. Lipoic acid is required for growth and $H^+$-ATPase activity is deficient.

In the present invention, the microorganism may possess any one of the aforementioned properties 1 to 3, and preferably possess property 3.

A microorganism having such properties can be obtained by giving the capability of producing L-valine or L-leucine to a microorganism belonging to the genus Escherichia, which is mutated so that it requires lipoic acid for growth and/or is deficient in $H^+$-ATPase, or by enhancing the capability of producing L-valine or L-leucine in the aforementioned mutant. The microorganism of the present invention can be also obtained by inducing a mutation whereby lipoic acid is required for growth and/or a mutation whereby $H^+$-ATPase is deficient in a microorganism belonging to the genus Escherichia.

The microorganism to be used in obtaining the aforementioned microorganisms can include a strain, which belongs to the genus Escherichia such as *Escherichia coli* (hereinafter, also referred to as *E. coli*) and exhibits no pathogenicity. For example, the following strains can be used.

*Escherichia coli* K-12 (ATCC10798)
*Escherichia coli* W3110 (ATCC27325)
*Escherichia coli* W1485 (ATCC12435)

In order to introduce a mutation whereby lipoic acid is required for growth and/or a mutation whereby $H^+$-ATPase is deficient into these microorganisms belonging to the genus Escherichia, the usual methods for introducing mutation, such as irradiation with X-ray or ultraviolet rays, or contact with mutagens including N-methyl-N'-nitro-N-nitrosoguanidine (hereinafter abbreviated as NG) and nitrous acid, can be applied. Additionally, the introduction of a mutation into a microorganism belonging to the genus Escherichia can be carried out by other genetic technique such as gene recombination, transduction, cell fusion and the like.

An example of the means for obtaining a mutant is as follows:

A mutant which requires lipoic acid for growth (hereinafter, referred to as a lipoic-acid-requiring strain) is obtained by culturing mutagenized bacterial cells on an agar plate, and by isolating colonies which exhibit lipoic acid requirement (A. A. Herbert and J. R. Guest: J. Gen. Microbiol., 53, 363–381 (1968)). As a lipoic acid requiring strain, specifically, *E. coli* W1485lip2 (ATCC25645) can be used.

A mutant which is deficient in $H^+$-ATPase (hereinafter, referred to as a $H^+$-ATPase-deficient strain) is obtained by selecting mutants which cannot grow on an agar plate containing citric acid as the sole carbon source and can grow on an agar plate containing glucose as the sole carbon source from mutagenized bacterial cells, and by further selecting, from these mutants, strains which do not exhibit $H^+$-ATPase activity. As a $H^+$-ATPase-deficient strain, specifically, *E coli* AN718 (*E. coli* Genetic Stock Center, Yale University, Department of Biology) can be used.

$H^+$-ATPase is a membrane-binding enzyme with approximately 500,000 KD in molecular weight, in which 8 types of subunits complicatedly associate, and functions to pump $H^+$ outside of cytoplasm through changes in the free energy caused by ATP hydrolyzation and to synthesize ATP utilizing a $H^+$-concentration gradient between the inside and outside of cytoplasmic membrane caused by intracellular respiration. Additionally, this enzyme is divided into an f0 fraction, which is localized on the inner membrane and exhibits $H^+$-transport activity, and an F1 fraction, which is localized in the membrane surface and catalyzes the decomposition and synthesis of ATP, and the F0 is composed of 3 types of subunits a, b and c, while the F1 is composed of 5 types of subunits $\alpha, \beta, \gamma, \delta, \epsilon$. A strain which has a mutation in any of these subunits can be used as a $H^+$-ATPase-deficient strain. The mutation of the $H^+$-ATPase deficiency may include the expression of a mutant subunit, and the non-expression of subunits comprising $H^+$-ATPase by the mutation at a promoter site.

Further, because oxidative phosphorylation is not carried out in a $H^+$-ATPase-deficient strain and energy is obtained by substrate-level phosphorylation, it is expected that the addition of various agents including $H^+$-ATPase inhibitors, TCA cycle inhibitors, respiratory chain inhibitors and uncoupling agents to the culture medium results in the same effect as $H^+$-ATPase deficiency. Such $H^+$-ATPase inhibitors include dicyclohexyl-carbodiimide, tributyltin, and aurovertin, TCA cycle inhibitors include malonic acid, monoiodoacetic acid, methyl violet and 2,4-dinitrophenol, electron transport inhibitors include thenoyltrifluoroacetone, 2-n-nonyl-4-hydroxyquinoline-N-oxide and antimycin, and uncoupling agents include valinomycin, atebrin and 4,5,6,7-tetrafluoro-2-trifluoromethylbenzimidazol. These inhibitors may be used either alone or as a mixture of more than two types of inhibitors.

The lipoic-acid-requiring strain obtained as above is additionally mutagenized as a parent strain for selecting an $H^+$-ATPase-deficient strain, or the $H^+$-ATPase-deficient strain is additionally mutagenized as a parent strain for selecting a strain which comes to require lipoic acid, whereby a mutant which exhibits both lipoic acid requirement and $H^+$-ATPase deficiency (hereinafter referred to as lipoic acid-requiring-$H^+$-ATPase-deficient strain) can be obtained. Further, the mutant which exhibits both lipoic acid requirement and $H^+$-ATPase deficiency can be obtained by introducing one of these mutations in a mutant which exhibits the other mutation by transduction, transformation, cell fusion and the like.

For example, lipoic acid-requiring-$H^+$-ATPase deficient strain can be obtained by transducing $H^+$-ATPase deficiency into a lipoic-acid-requiring strain as a parent strain. In this case, the aforementioned W1485lip2 strain can be used as a parent strain, and the aforementioned AN718 strain can be used as a donor strain. The lipoic acid-requiring-$H^+$-ATPase-deficient strain can be obtained by transducing a lipoic acid requirement into a $H^+$-ATPase-deficient strain as a parent strain.

The lipoic acid-requiring-$H^+$-ATPase-deficient strain can include *E. coli* AJ12631. The strain AJ12631 has been deposited on Jul. 24, 1991 in National Institute of Bioscience and Human Technology of Agency of Industrial Science and Technology under an accession number of FERM P-12381, transferred to international deposition based on the Budapest Treaty on Aug. 29, 1995, and deposited under an accession number of FERM BP-5209.

A microorganism of the present invention can be obtained by giving the capability of producing L-valine or L-leucine to a lipoic acid requiring mutant, a $H^+$-ATPase-deficient mutant or a lipoic acid-requiring-$H^+$-ATPase-deficient mutant belonging to the genus Escherichia, or by enhancing the capability of producing L-valine or L-leucine in the aforementioned mutants. Additionally, the microorganism of the present invention can be also obtained by introducing a lipoic acid requirement and/or $H^+$-ATPase deficiency in a microorganism belonging to the genus Escherichia having the capability of producing L-valine or L-leucine. Further, even for a microorganism being low in the capability of producing L-valine or L-leucine, this capability can be enhanced by introducing a lipoic acid requirement and/or $H^+$-ATPase deficiency.

(1) L-valine-producing microorganism

An L-valine-producing microorganism can be obtained by giving the capability of producing L-valine to a lipoic-acid-requiring mutant, a $H^+$-ATPase-deficient mutant, or a lipoic acid-requiring-$H^+$-ATPase-deficient mutant of a microorganism belonging to the genus Escherichia, or by enhancing the capability of producing L-valine in the aforementioned mutant.

The giving or enhancing of the capability of producing L-valine is carried out, for example, by introducing genes for L-valine biosynthesis, whose regulatory mechanism is substantially released, into a microorganism belonging to the genus Escherichia. A mutation which leads to the suppression of the regulatory mechanism of the genes for the L-valine biosynthesis of the microorganism belonging to the genus Escherichia, may be introduced.

In a microorganism belonging to the genus Escherichia, the final step of L-valine biosynthesis is carried out by a group of ilvGMEDA operon-encoded enzymes. The ilvGMEDA operon includes each of ilvG, ilvM, ilvE, ilvD and ilvA genes, which encodes a large subunit and a small subunit of isozyme II of acetohydroxy-acid synthase, transaminase, dihydroxy-acid dehydratase and threonine deaminase, respectively. Of these enzymes, acetohydroxy-acid synthase, transaminase and dihydroxy-acid dehydratase catalyze the synthetic pathways from pyruvic acid to L-valine and from 2-ketobutyric acid to L-isoleucine, and threonine deaminase catalyzes the deamination from L-threonine to 2-ketobutyric acid, which is a rate-limiting step of L-isoleucine biosynthesis. Therefore, to conduct the reaction of L-valine synthesis so that it proceeds efficiently, an operon which does not express active threonine deaminase is used preferably. As such ilvGMEDA operons, an ilvGMEDA operon in which a mutation leading to the production of an inactivated threonine deaminase is introduced to ilvA or ilvA is destroyed, or an ilvGMED operon in which ilvA is deleted, can be used.

Because of the regulation of the expression (attenuation) of an ilvGMEDA operon by L-valine and/or L-isoleucine and/or L-leucine, the region necessary for the attenuation is preferably deleted or mutated to release the regulation of the expression caused by the generating L-valine.

The aforementioned ilvGMEDA operon, which does not express threonine deaminase activity and whose attenuation is released, can be obtained by mutating a wild-type ilvGMEDA operon or modifying it with genetic recombination techniques.

The ilvGMEDA operon can include an operon derived from a microorganism belonging to the genus Escherichia, and particularly an ilvGMEDA operon derived from E. coli. Among microorganisms belonging to the genus Escherichia, the microorganism to be used is not particularly limited, however specifically, microorganisms described by Neidhardt, F. C. et al. (*Escherichia coli* and *Salmonella typhimurium*, American Society for Microbiology, Washington D.C., 1208, Table 1) can be utilized. When a wild-type strain is used as the donor strain of DNA including an ilvGMEDA operon, DNA including a wild-type ilvGMEDA operon is obtained.

However, when E. coli is used as the DNA donor strain of a wild-type ilvGMEDA operon, a wild-type K-12 strain does not express active isozyme II of acetohydroxy acid synthase (AHASII) because an ilvG gene possesses a frameshift mutation (Proc. Natl. Acad. Sci. USA, 78, 922, 1991). Therefore, when the K-12 strain is used as the DNA donor strain, it is necessary that a mutant, in which the frame is restored so as to recover the activity of the ilvG gene-encoded acetohydroxy-acid synthase, is prepared, and then used as the DNA donor strain. Otherwise, by using E. coli, other than a strain derived from the K-12 strain, as a DNA donor, only the ilvG gene may be isolated and introduced in ilvGMEDA operon derived from the K-12 strain. Thus, the ilvMEDA region is isolated from the K-12 strain as a DNA donor, only the ilvG gene is isolated from E. coli, other than a strain derived from the K-12 strain, as a DNA donor, and the obtained both sequences are ligated together to form the full-length ilvGMEDA operon. The isozyme II of acetohydroxy-acid synthase (AHASII) is composed of two different large and small subunits. The large subunit is encoded by a ilvG gene. The small subunit is encoded by a ilvM gene.

The method of obtaining the ilvGMEDA operon which is released from the attenuation may be as follows:

The localization and DNA sequences of the attenuator which is 5'-upstream in the ilvGMEDA operon have been reported by R. P. Lawther et al. (Nucleic Acids Res., 15, 2137 (1987)).

Starting from ilvGMEDA which does not express active threonine deaminase, an ilvGMEDA operon wherein active threonine deaminase is not expressed and attenuator is deleted is obtained by preparing an ilvGMEDA operon wherein the attenuator is deleted.

The nucleotide sequence shown in SEQ ID NO:1 is a sequence including the promoter, the attenuator and the ilvG gene-coding region among nucleotide sequences of the ilvGMEDA operon and includes a region necessary for attenuation. An amino acid sequence coded by the ilvG gene is shown in SEQ ID NO:2. Nucleotides 966 to 971 of the DNA sequence encode two consecutive leucine residues localized in the leader peptide, nucleotides 999 to 1007 of the DNA sequence encode three consecutive valine residues localized in the leader peptide, and nucleotides 1008 to 1016 of the DNA sequence encode three consecutive isoleucine residues localized in the leader peptide. Nucleotides 1081 to 1104 of the DNA sequence encode a portion forming a rho-independent terminator-like stem-loop structure in the attenuator.

Sufficient amounts of L-isoleucine, L-valine and L-leucine in a cell lead to the formation of the rho-independent terminator-like stem-loop structure with the RNA which is a transcript encoded by nucleotides 1081 to 1104 of the DNA sequence so that RNA polymerase terminates transcription, which represses the expression of the ilvGMEDA operon.

For example, the shortage of L-valine in a cell results in the shortage of L-valine-binding tRNA, which causes ribosomal translation to be retarded at consecutive valine residues localized in the region encoding the leader peptide. This leads to the formation of an additional mRNA configuration in the three-dimensional structure, resulting in the formation of rho-independent terminator-like stem-loop structure in the RNA, which is stimulated by the transcription of nucleotides 1081 to 1104 the DNA sequence, is repressed. Thus, RNA polymerase continues transcription, which results in the expression of the ilvGMEDA operon. Similarly, the shortage of L-isoleucine or L-leucine leads to the expression of ilvGMEDA operon.

Therefore, to delete the region necessary for attenuation by L-valine, nucleotides 999 to 1007 or 1081 to 1104 of the DNA sequence shown in SEQ ID NO:1 may be deleted. Similarly, to delete the region necessary for attenuation by L-leucine in the production of L-leucine-producing microorganism as described below, nucleotides 966 to 971 or 1081 to 1104 of the DNA sequence disclosed in SEQ ID NO:1 may be deleted.

The deletion of the region necessary for attenuation means that the introduced mutation releases the attenuation. Therefore, this mutation is not limited to only the deletion of all attenuators which are upstream in the ilvGMEDA operon. Thus, the mutation may cause the attenuator not to form a rho-independent terminator-like stem-loop structure. Additionally, in the production of L-valine producing microorganism, the mutation may cause the leader peptide not to contain consecutive valine residues. Furthermore, in the production of L-leucine-producing microorganism, the mutation may cause the leader peptide not to contain consecutive leucine residues. Attenuation does not function in any of the aforementioned cases.

Thus, concepts of this deletion of the region necessary for attenuation include the insertion of an additional DNA fragment into the attenuator as well as the deletion of all parts or vicinities of attenuators which are 5'-upstream in the ilvGMEDA operon.

(i) Isolation of wild-type ilvGMEDA operon

To isolate a DNA containing the ilvGMEDA operon, the method, wherein ilvGM, ilvE, ilvD and ilvA genes are each isolated and then ligated, may be suggested. However, in the construction of an L-valine-producing microorganism, an ilvA gene encoding threonine deaminase is not necessary, so that ilvGM, ilvE and ilvD genes may be ligated to obtain a DNA including the ilvGMED.

First, E. coli, e.g. E. coli K-12, E. coli W3110, E. coli MC1061 (all of which include a frameshifted ilvG, E. coli MI162 (thr-10, car-94, $\lambda^-$, relA1, ilvG603, thi-1) or E. coli B (the latter two of which include a normal ilvG), is cultured to obtain the cultured cells. The microorganism may be cultured by the usual solid medium method, and preferably cultured according to the liquid medium method in consideration of efficiency in cell harvesting. A medium wherein yeast extracts, pepton, trypton or meat extracts are added to sodium chloride (NaCl) is to be used. Specifically, L-broth (Bacto-trypton 1%, Bacto-yeast extracts 0.5%, NaCl 0.5%, glucose 0.1%, pH 7.2) is to be used. The initial pH of the medium is preferably adjusted to 6–8. The cultivation is conducted at 30 to 42° C., preferably about 37° C., for 4–24 hours, with aeration, stirring and submerged in culture, with a shaking culture, or with a stationary culture. *E. coli* MI162 is available from the *E. coli* Genetic Stock Center (Connecticut, U.S.A.). The ID No. of this strain is CGSC5919. The detail characteristics of this strain are described in Mol. Gen. Genet., 143, 243 (1976), and J. Bacteriol., 149, 294 (1982).

Thus, the obtained culture is centrifuged, e.g. at 3,000 r.p.m. for 5 minutes to obtain a pellet of *E. coli*. From this pellet, chromosomal DNA can be obtained by the method of Saitoh and Miura (Biochem. Biophys. Acta., 72, 619 (1963)) or K. S. Kirby (Biochem. J., 64, 405 (1956)).

To isolate the ilvGMEDA operon from the resulting chromosomal DNA, the chromosomal DNA library is prepared. First, the chromosomal DNA is partially digested by a proper restriction enzyme to obtain a mixture of different DNA fragments. A wide variety of restriction enzymes can be used if the digestion reaction is adjusted for the degree of digestion. For example, the chromosomal DNA is digested with Sau3AI at not less than 30° C., preferably at 37° C., at an enzyme concentration of 1–10 units/ml for a varying period of time (1 minute to 2 hours).

Subsequently, the digested DNA was ligated to vector DNA which allows autonomous replication to prepare recombinant DNA. Specifically, the vector DNA is completely digested and cleaved with the restriction enzyme, e.g. BamHI, which generates the restriction termini identical to those generated by Sau3AI used in the digestion of the chromosomal DNA, at a temperature of above 30° C., at a enzyme concentration of 1–100 units/ml for above 1 hour, preferably 1–3 hours. And then, the chromosomal DNA fragments and the cleaved vector DNA, obtained as mentioned above, were mixed, added to DNA ligase, preferably T4 DNA ligase, and reacted at a temperature of 4–16° C., at a enzyme concentration of 1–100 units/ml above 1 hour, preferably 6–24 hours to obtain recombinant DNA.

Using the resulting recombinant DNA, a microorganism belonging to the genus Escherichia, for example, a mutant which is deficient in acetohydroxy acid synthase activity such as *E. coli* MI262 (leuB6, ilvI614, ilvH612, $\lambda^-$, relA1, spoT1, ilvB619, ilvG603, ilvG605(am), thi-1), transaminase B-deficient mutants such as *E. coli* AB2070 (proA2, trp-3, hiaG4, ilvE12, metE12, metE46, thi-1, ara-9, lac-Y1 or lacZ4, galK2, malA1, mtl-1, rpsL8 or rpsL9, ton-1, tsx-3, $\lambda^R$, $\lambda^-$, supE44), or dihydroxy acid dehydratase-deficient mutants such as *E. coli* AB1280 (hisG1, ilvD16, metB1, argH1, thi-1, ara-13, lacY1 or lacZ4, gal-6, xyl-7, mtl-2, malA1, repsL8, 9, or 12, tonA2, $\lambda^R$, $\lambda^-$, supE44), is transformed to prepare chromosomal DNA library. This transformation can be performed by the method of D. M. Morrison (Methods in Enzymology 68, 326, 1979) or a method wherein the treatment of a recipient cell with calcium chloride increases the permeability of DNA (Mandel, M. and Higa, A., J. Mol., Biol., 53, 159 (1970). *E. coli* MI262 is available from the *E. coli* Genetic Stock Center (Connecticut, U.S.A.). The ID No. of this strain is CGSCS769. The detailed characteristics of this strain are described in Mol. Gen. Genet., 156, 1 (1977). *E. coli* AB2070 is available from the *E. coli* Genetic Stock Center (Connecticut, U.S.A.). The ID No. of this strain is CGSC2070. The detailed characteristics of this strain are described in J. Bacteriol., 109, 730 (1972).

Because the nucleotide sequence of the full-length ilvGMEDA operon has been reported (Nucleic Acids Res., 15, 2137 (1987)), a certain length of DNA fragments including the aimed gene can be prepared by digesting the chromosomal DNA with a specific restriction enzyme. Only DNA fragments of a certain length are ligated to the vector DNA to generate recombinant DNA and to prepare the chromosomal DNA library, whereby the DNA fragment including the aimed gene can be obtained more efficiently.

From the obtained chromosomal DNA library, the strain which has recombinant DNA including the ilvGM gene is obtained by selecting a strain having increased acetohydroxy acid synthase activity or a strain whose nutrient requirement caused by the deficient in acetohydroxy acid synthase gene is complemented.

From the obtained chromosomal DNA library, the strain which has recombinant DNA including an ilvE gene is obtained by selecting a strain having increased transaminase B activity or a strain whose nutrient requirement caused by the deficiency in the transaminase B gene is complemented.

From the obtained chromosome DNA library, the strain which has recombinant DNA including an ilvD gene is obtained by selecting a strain having increased dihydroxy acid dehydratase activity or a strain whose nutrient requirement caused by the deficiency in the dihydroxy acid dehydratase gene is complemented.

To examine whether candidates to have recombinant DNA including the ilvGM gene have recombinant DNA wherein ilvGM gene is cloned or not, increase of acetohydroxy acid synthase activity is confirmed by preparing a cell extract from the candidate and further preparing a crude enzyme solution from this extract. The assay of acetohydroxy acid synthase activity can be performed by the method of M. D. Felice et al. (Methods in Enzymology 166, 241).

Because the AHAS-deficient strain exhibits isoleucine, leucine and valine requirements, when the acetohydroxy acid synthase-deficient mutant is used as a host cell, DNA fragments including the ilvGM gene can be obtained by isolating a strain which can grow in a minimum medium without valine, and by collecting recombinant DNA from said strain.

Otherwise, DNA sequence containing the ilvGM gene has been reported by R. P. Lawther et al. (Nucleic Acids Res., 15, 2137 (1987)). Thus, the confirmation can be performed by isolating the recombinant DNA from the candidates, by sequencing and comparing it with that described in the report.

As described above, there is a mutation within the open reading frame of the ilvG gene of *E. coli* K-12. As a result, the generated frameshift and further the emergence of a termination codon cause translational termination. Thus, the termination codon emerges at a position of 982–984 downstream of the initiation codon ATG (at a position of 1–3) of the ilvG gene. Therefore, when the ilvGM gene obtained from the strain is used, the mutation region needs to back to the normal sequence by the site-directed mutagenesis method. For example, for the ilvG gene (ilvG603) of *Escherichia coli* MI162, the frame is normalized by placing two base pairs of TG before the termination codon TGA at a position of 982–984. The other mutations are described in FIG. 2 in J. Bacteriol., 149, 294 (1982).

The method for confirming whether candidates to have recombinant DNA including the ilvE gene have recombinant DNA wherein ilvE gene is cloned or not is as follows. Because the transaminase B-deficient mutant exhibits an isoleucine requirement, when the transaminase B-deficient mutant is used as a host cell, DNA fragments including the ilvE gene can be obtained by isolating a strain which can grow in a minimum medium without isoleucine, and by collecting recombinant DNA from said strain.

Otherwise, the DNA sequence including the ilvE gene has been reported by R. P. Lawther et al. (Nucleic Acids Res., 15, 2137 (1987)). Thus, the confirmation can be performed by isolating the recombinant DNA from the candidates, by sequencing and comparing it with that described in the report.

The method for confirming whether candidates to have recombinant DNA including the ilvD gene have recombinant DNA wherein ilvD gene is cloned or not is as follows. Because the dihydroxy acid dehydratase-deficient mutant exhibits an isoleucine, leucine and valine requirement, when the dihydroxy acid dehydratase-deficient mutant is used as a host cell, DNA fragments including the ilvD gene can be obtained by isolating a strain which can grow in a minimum medium without valine, and by collecting recombinant DNA from said strain.

Otherwise, the DNA sequence including the ilvD gene has been reported by R. P. Lawther et al. (Nucleic Acids Res., 15, 2137 (1987)). Thus, the confirmation can be performed by isolating the recombinant DNA from the candidates, by sequencing and comparing it with that described in the report.

From each of the aforementioned strains, recombinant DNA can be isolated e.g. by the methods of P. Guerry et al. (J. Bacteriol., 166, 1064 (1973)) and D. B. Clewell (J. Bacteriol., 110, 667 (1972)).

To obtain a full-length ilvGMEDA operon, a DNA fragment including the ilvGM gene, a DNA fragment including the ilvE gene, and a DNA fragment including the ilvD gene are ligated. In the ligation, the DNA sequence of the full-length ilvGMEDA described by R. P. Lawther (Nucleic Acids Res., 15, 2137 (1987)) can be used as a reference.

A wild-type ilvGMEDA operon may be obtained by preparing chromosomal DNA from a strain having the wild-type ilvGMEDA in its chromosome by the method of Saitoh and Miura, and by amplifying the ilvGMEDA operon by the polyrmrase chain reaction method (PCR; see White, T. J. et al.; Trends Gent., 5, 185 (1989)). As a DNA primer in amplification, those complementary to both 3'-ends of DNA double strands including all or a part of the region of ilvGMEDA operon are used. In the amplification of only a part of the region of the ilvGMEDA operon, DNA fragments including the entire region are screened by using said DNA fragment as a probe. In the amplification of the entire region of the ilvGMEDA operon, an agarose gel electrophoresis of a PCR solution which contains DNA fragments including the amplified ilvGMEDA operon followed by extraction of the aimed DNA fragments allows for the collection of DNA fragments including the ilvGMEDA operon. Because in this case, also, the ilvA gene is not essential to the construction of a L-valine-producing microorganism, only the ilvGMED may be amplified.

When preparing a DNA primer, the DNA sequence of the full-length ilvGMEDA operon described by R. P. Lawther et al. (Nucleic Acids Res., 15, 2137 (1987)) can be used as a reference.

Primer DNA can be synthesized in a commercially available DNA synthesizer (e.g. Applied Biosystems, DNA synthesizer model 380B) by the phosphoramidite method (Tetrahedron Letters, 22, 1859 (1981)). PCR can be performed in a commercially available PCR system (Perkin Elmer, DNA thermal cycler PJ2000), using Taq DNA polymerase (supplied by Takara Shuzo, Ltd.) according to the method indicated by suppliers.

The ilvGMEDA operon amplified by the PCR method is ligated to vector DNA, which allows autonomous replication, in the cell of the microorganism belonging to the genus Escherichia and induced into the cell of a microorganism belonging to the genus Escherichia, whereby the induction of a mutation into the ilvA gene and the deletion of the region necessary for attenuation are facilitated. The vector DNA, transformation method, and further confirmation of the ilvGMEDA operon are the same as described above.

When E. coli K-12, E. coli W3110 and E. coli MC1061 are used as the donor microorganism of the ilvGMEDA operon, because a frameshift mutation is present within the open reading frame of the ilvG gene, this mutation needs to be normalized by the site-directed mutagenesis method. When E. coli MI162 (thr-10, car-94, $\lambda^-$, relA1, ilvG603, thi-1) and E. coli B are used as the donor microorganism of the ilvGMEDA operon, the ilvG gene can be used as it is.

(ii) Deletion of the region of ilvGMEDA operon necessary for attenuation

Concepts of the deletion of the region necessary for attenuation from ilvGMEDA include an insertion of an additional DNA fragment into the attenuator as well as a deletion of all of, a part of or an area surrounding the attenuator which is upstream in the ilvGMEDA operon. Herein, the "attenuator" means a DNA sequence which forms a rho-independent terminator-like stem-loop structure. For example, the sequence corresponds to nucleotides 1081 to 1104 of the DNA sequence shown in SEQ ID NO:1.

To delete the attenuator, DNA fragments upstream and downstream of the attenuator in the ilvGMEDA operon may be each prepared to ligate the both DNA fragments. For example, the DNA fragment upstream of the attenuator in the ilvGMEDA operon can be prepared by cleaving a DNA fragment including the full length of the ilvGMEDA operon with a proper restriction enzyme. Otherwise, the DNA fragment upstream of the attenuator in the ilvGMEDA operon may be amplified by the PCR method. The primer DNA used in the PCR method may be chemically synthesized on the basis of the DNA sequences described by R. P. Lawther et al. (Nucleic Acids Res., 15, 2137 (1987)) and G. Coopola et al. (Gene, 97, 21 (1991)). Furthermore, the DNA fragment upstream of the attenuator in the ilvGMEDA operon may be chemically synthesized.

The method for preparing the DNA fragment downstream of the attenuator in the ilvGMEDA operon is similar to that above.

Starting from the ilvGMEDA operon, the ilvGMEDA operon wherein part or vicinity of the attenuator is deleted may be prepared. Because the location and DNA sequence of the attenuator have been reported by R. P. Lawther et al. (Nucleic Acids Res., 15, 2137 (1987)), DNA to be deleted is determined on the basis of the sequence.

The DNA to be deleted is preferably the DNA sequence which is necessary to form a rho-independent terminator-like stem-loop structure, and/or includes the region encoding consecutive valine residues which are upstream in the stem-loop structure. To delete a part of or an area around the attenuator, DNA fragments upstream and downstream of the attenuator in the ilvGMEDA operon may be each prepared to ligate both DNA fragments. For example, the DNA fragment upstream in the attenuator of the ilvGMEDA operon can be prepared by cleaving a DNA fragment including the full length of the ilvGMEDA operon with a proper restriction enzyme. Otherwise, the DNA fragment upstream of the DNA to be deleted in the ilvGMEDA operon may be amplified by the PCR method. The primer DNA used in the PCR method may be chemically synthesized on the basis of the DNA sequences described by R. P. Lawther et al. (Nucleic Acids Res., 15, 2137 (1987)) and G. Coopola et al. (Gene, 97, 21 (1991)). Furthermore, the DNA fragment upstream of the DNA to be deleted in the ilvGMEDA operon may be chemically synthesized.

The method for preparing the DNA fragment downstream of the DNA to be deleted in the ilvGMEDA operon is similar to that above.

Starting from the ilvGMEDA operon, an ilvGMEDA operon wherein an additional DNA fragment is inserted into the attenuator may be prepared. Because the location and DNA sequence of the attenuator have been reported by R. P. Lawther et al. or G. Coppola et al., the position of the insertion and the DNA sequence of an additional DNA fragment to be inserted are determined on the basis of the sequence.

The additional DNA fragment to be inserted is preferably inserted into the DNA sequence which is necessary to form a rho-independent terminator-like stem-loop structure, or into the DNA region encoding consecutive valine residues which is upstream of the stem-loop structure. As a result of the insertion, the attenuator can not form a rho-independent terminator-like stem-loop structure and so the attenuator is expected to loose its function.

The DNA sequence of the additional DNA fragment to be inserted is preferably designed not to form a rho-independent terminator-like stem-loop structure, and to cause the consecutive valine residues not to be present upstream of the rho-independent terminator-like stem-loop structure when inserted.

To insert an additional DNA fragment into the attenuator, the DNA fragment of the ilvGEMED operon which is upstream of the additional DNA fragment to be inserted, the DNA fragment of the ilvGEMED operon which is downstream of the additional DNA fragment to be inserted, and the additional DNA fragment to be inserted may be prepared to ligate these three DNA fragments. For example, the DNA fragment upstream of the additional DNA fragment in the ilvGMEDA operon can be prepared by cleaving a DNA fragment including the full length of the ilvGMEDA operon with a proper restriction enzyme. Otherwise, the DNA fragment of the ilvGMEDA operon which is upstream of the additional DNA fragment may be amplified by the PCR method. The primer DNA used in the PCR method may be chemically synthesized on the basis of the DNA sequences described by R. P. Lawther et al. (Nucleic Acids Res., 15, 2137 (1987)) and G. Coopola et al. (Gene, 97, 21 (1991)). Furthermore, the DNA fragment upstream of the additional DNA fragment in the ilvGMEDA operon may be chemically synthesized.

The method for preparing the DNA fragment downstream of the additional DNA fragment in the ilvGMEDA operon is similar to that above.

The additional DNA fragment to be inserted can be prepared by chemical synthesis.

In the amplification of the DNA fragment of the ilvGMEDA operon which is upstream of the DNA region into which the additional DNA fragment, or the DNA fragment of the ilvGMEDA operon which is downstream of the DNA region into which the additional DNA fragment, the additional DNA fragment to be inserted can be ligated with the primer DNA. For example, the 3'-end DNA primer used for the amplification of the DNA fragment upstream of the DNA region into which the additional DNA fragment is ligated with one of the strands of the additional DNA fragment to be inserted. Similarly, the 5'-end DNA primer used for the amplification of the DNA fragment downstream of the DNA region into which the additional DNA fragment is ligated with the complementary one of the strands of the additional DNA fragment to be inserted. Two different DNA fragments which have been amplified using above-mentioned primers are ligated.

(iii) Inactivation of threonine deaminase

When the obtained ilv operon contains an ilvA gene, the ilvA is deleted, or modified to cause a mutation, insertion and deletion within the ilvA so as to inactivate the expressed threonine deaminase. As a modification, for example, a restriction site in the ilvA gene can be cleaved to delete a DNA fragment which is downstream in the cleaved site. A DNA fragment may be cut out by cleaving the ilvA gene at two sites and then re-ligating it. Further, the expressed threonine deaminase can be inactivated by inserting another DNA fragment such as a synthesized DNA into the restriction site. When the restriction sites are cohesive ends, these cohesive ends are treated so as to be blunt ends, and then the resulting ends are ligated together, whereby the expressed threonine deaminase can be inactivated. Furthermore, the expressed threonine deaminase can be inactivated by site-specific mutagenesis and the like.

Hereinafter, the ilvGMEDA operon, wherein attenuation is repressed and the threonine deaminase activity is not expressed, or ilvA is deleted, is referred to as a derepressed ilvGMEDA* operon, where A* represents the deleted ilvA gene, or the ilvA encoding inactivated threonine deaminase or a part thereof.

(iv) Introduction of derepressed ilvGMEDA* operon in a microorganism belonging to the genus Escherichia A DNA fragment including the derepressed ilvGMEDA* operon obtained as above used as a recombinant DNA, introduced into a proper host microorganism and expressed, whereby the microorganism, in which the expression of the enzymes involving valine biosynthesis encoded by the ilvGMEDA* operon is enhanced, can be obtained. As a host microorganism, a microorganism belonging to the genus Escherichia, e.g. *Escherichia coli*, is preferably used.

A derepressed ilvGMEDA* operon, which is cut out from a recombinant DNA and inserted into the other vector DNA, may be used. As the vector DNA which can be used in the present invention, for example, pUC19, pUC18, BR322, pHSG299, pHSG298, pHSG399, pHSG398, RSF1010, pMW119, pMW118, pMW219 and pMW218 can be used. Additionally, a vector of phage DNA also can be used.

Further, to efficiently perform the expression of the derepressed ilvGMEDA* operon, the other promoters, which act in a microorganism including lac, trp and $P_L$, may be ligated, and the promoter innate to the ilvGMEDA* operon may be used as it is or after amplification.

As mentioned above, the DNA fragment including the derepressed ilvGMEDA* operon may be present in a host microorganism as an extrachromosomal DNA such as a plasmid by inserting the operon into vector DNA which allows autonomous replication into the host, while the derepressed ilvGMEDA* operon may be inserted into the chromosome of the host microorganism by using the techniques of transduction, a transposon (Berg, D. E. and Berg, C. M., Bio/Technol., 1, 417 (1983)), a Mu phage (Japanese Patent Application Laid-Open No. 2-109985(1990)) or by homologous recombination (Experiments in Molecular Genetics, Cold Spring Habor Lab. (1972)). The number of the derepressed ilvGMEDA* operons introduced into the host may be either one or more.

As described above, an L-valine producing microorganism can be obtained by introducing the DNA fragment including the derepressed ilvGMEDA* operon into a lipoic acid requiring and/or $H^+$-ATPase-deficient microorganism belonging to the genus Escherichia. Also, an L-valine-producing microorganism can be obtained by introducing lipoic acid requirement and/or $H^+$-ATPase deficiency to a microorganism belonging to the genus Escherichia and carrying the DNA fragment including the derepressed ilvGMEDA* operon.

(2) L-leucine-producing microorganism

As illustrated in the example below, it is found that a lipoic acid-requiring or H$^+$-ATPase-deficient microorganism belonging to the genus Escherichia can increase the L-valine productivity. This finding suggests that a lipoic acid-requiring mutation or H$^+$-ATPase-deficient mutation causes the intracellular metabolism to stimulate the L-valine synthesis. Therefore, the lipoic acid requiring mutation or H$^+$-ATPase-deficient mutation is considered to promote L-leucine biosynthesis whose synthetic pathway branches out from the final intermediate of L-valine. Thus, if the capability of producing L-leucine is added to or enhanced in a lipoic acid-requiring mutant, a H$^+$-ATPase-deficient mutant, or a lipoic acid-requiring and H$^+$-ATPase-deficient mutant, the capability of producing L-leucine is expected to be added thereto or enhanced.

The addition or enhancement of the capability of producing L-leucine, for example, is performed by introducing an L-leucine biosynthetic gene, wherein the regulatory mechanism is substantially released, into a microorganism belonging to the genus Escherichia, in addition to the properties necessary for the production of L-valine. And a mutation, whereby the regulatory mechanism of L-leucine biosynthesis in a microorganism belonging to the genus Escherichia is substantially released, may be introduced. These genes can include, for example, a leuA gene in which inhibition by L-leucine is substantially released.

In addition to the aforementioned capability of producing L-valine or L-leucine, a microorganism of the present invention may have the known characteristics which are effective in enhancing its capability of producing an amino acid, for example, various nutrient requirements, resistance to drugs, sensitivity to drugs, and drug dependence, or characteristics wherein a gene promoting the biosynthesis of an amino acid is amplified by means of gene engineering.

<2> Production of L-valine or L-leucine of the present invention

The production of L-valine or L-leucine of the invention can be performed by culturing the microorganism of the present invention in a liquid medium, to allow L-valine or L-leucine to be produced and accumulated in the liquid medium, and collecting L-valine or L-leucine from this liquid medium. In this production, the L-valine-producing microorganism of the present invention is used in the production of L-valine, and the L-leucine producing microorganism of the present invention is used in the production of L-leucine.

In the producing method of the present invention, the cultivation of the L-valine or L-leucine-producing microorganism, the collection and purification of L-valine or L-leucine from the liquid medium may be performed in a manner similar to the conventional fermentation method wherein an amino acid is produced using a microorganism. A medium used for culture may be either a synthetic medium or a natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium carbonate, etc. are used.

The cultivation is performed preferably under aerobic conditions such as a shake culture, and an aeration and stirring culture, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the target L-valine or L-leucine in the liquid medium.

After cultivation, solids such as cells can be removed from the liquid medium by centrifugation and membrane filtration, and then the target L-valine or L-leucine can be collected and purified by ion-exchange, concentration and crystallization methods.

BEST MODE OF CARRYING OUT THE INVENTION

Figure 1:
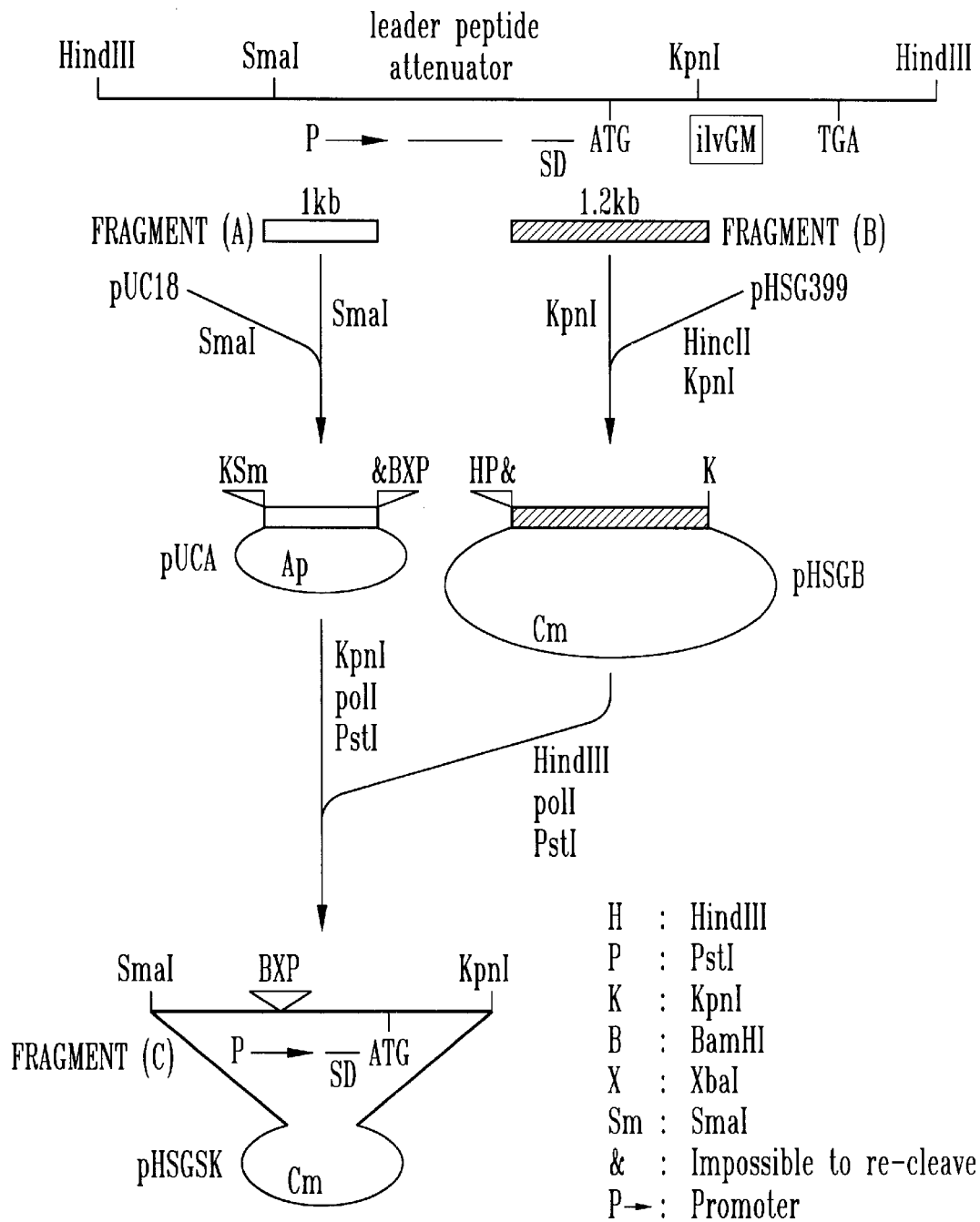
FIG. 1 is a scheme of the construction of the plasmid pHSGSK.

The invention is described with reference to the following example:

EXAMPLE 1

Creation of L-valine-producing microorganism

<1> Construction of pMWdAR6 carrying the derepressed ilvGMEDA* operon

The chromosomal DNA was extracted from *Escherichia coli* MI162. The chromosomal DNA was cleaved with restriction enzyme HindIII. The length of a HindIII—HindIII DNA fragment including ilvGM genes was found to be 4.8 kb. Therefore, the HindIII—HindIII DNA fragment with approximately 4.8 kb and the DNA fragment obtained by digestion of the plasmid vector pBR322 (purchased form Takara Shuzo, Co., Ltd.) with HindIII, were ligated.

The resulting DNA-ligated mixture was induced into *Escherichia coli* MI162 which is an acetohydroxy-acid synthase-deficient strain. The strains in which the deficiency of acetohydroxy-acid synthase was complemented by transformation were selected and the plasmid structure was isolated from the selected strains. The results of the analysis of the plasmid revealed that a 4.8-kb DNA fragment containing the ilvGM gene and a portion of 5'-terminal of ilvE gene was inserted into the HindIII site of the pBR322. The plasmid was termed pBRGM7.

The synthetic oligonucleotides shown in SEQ ID NO:3 and NO:4 were synthesized with reference to the DNA sequence of the ilvGM gene described in Gene, 97, 21, (1991), Pro. Natl. Acad. Sci. U.S.A., 78, 922, (1981) and J. Bacteriol., 149, 294, (1982). DNA was amplified by the PCR method, using both synthesized DNAs as a primer and chromosomal DNA of MI162 strain as a template. The amplified DNA fragment included nucleotides 25 to 952 of the nucleotide sequence shown in SEQ ID NO:1. The fragment was termed Fragment (A).

Similarly, the synthetic oligonucleotides shown in SEQ ID NO:5 and NO:6 were synthesized with reference to the DNA sequence described in Gene, 97, 21, (1991), Pro. Natl. Acad. Sci. U.S.A., 78, 922, (1981) and J. Bacteriol., 149, 294, (1982). DNA was amplified by the PCR method, using both synthesized DNAs as a primer and chromosomal DNA of the MI162 strain as a template. The amplified DNA fragment included nucleotides 1161 to 2421 of the nucleotide sequence shown in SEQ ID NO:1. The fragment was termed Fragment (B).

The plasmid pUCA was prepared by ligating the large fragment obtained by digestion of Fragment (A) with SmaI and the DNA fragment obtained by digestion of the vector, pUC18 (Takara Shuzo, Co., Ltd.) with SmaI. The plasmid pHSGB was prepared by ligating the large fragment obtained by digestion of Fragment (B) with KpnI and the DNA fragment obtained by digestion of the vector, pHSG399 (Takara Shuzo, Co., Ltd.) with HincII and KpnI.

The plasmid pUCA was digested with KpnI, the blunt-end fragment was prepared with the large fragment of DNA polymerase I (Klenow fragment), and digested with PstI, and finally, a DNA fragment containing Fragment (A) was isolated. Plasmid pHSGB was digested with HindIII, the blunt-end fragment was prepared with the large fragment of DNA polymerase I (Klenow fragment), and digested with PstI, and finally, a DNA fragment containing Fragment (B) was isolated. The plasmid pHSGSK was prepared by ligating both DNA fragments.

The SmaI-KpnI fragment derived from Fragments (A) and (B) in pHSGSK was termed Fragment (C). Fragment (C) corresponded to a fragment obtained by digestion of a 4.8-kb HindIII—HindIII fragment with SmaII and KpnI, contained a promoter, the SD sequence and a upstream region of the ilvG gene, but lost the DNA sequence of 0.2 kb from a leader sequence to an attenuator. The scheme of construction of pHSGSK is summarized in FIG. 1.

Figure 2:
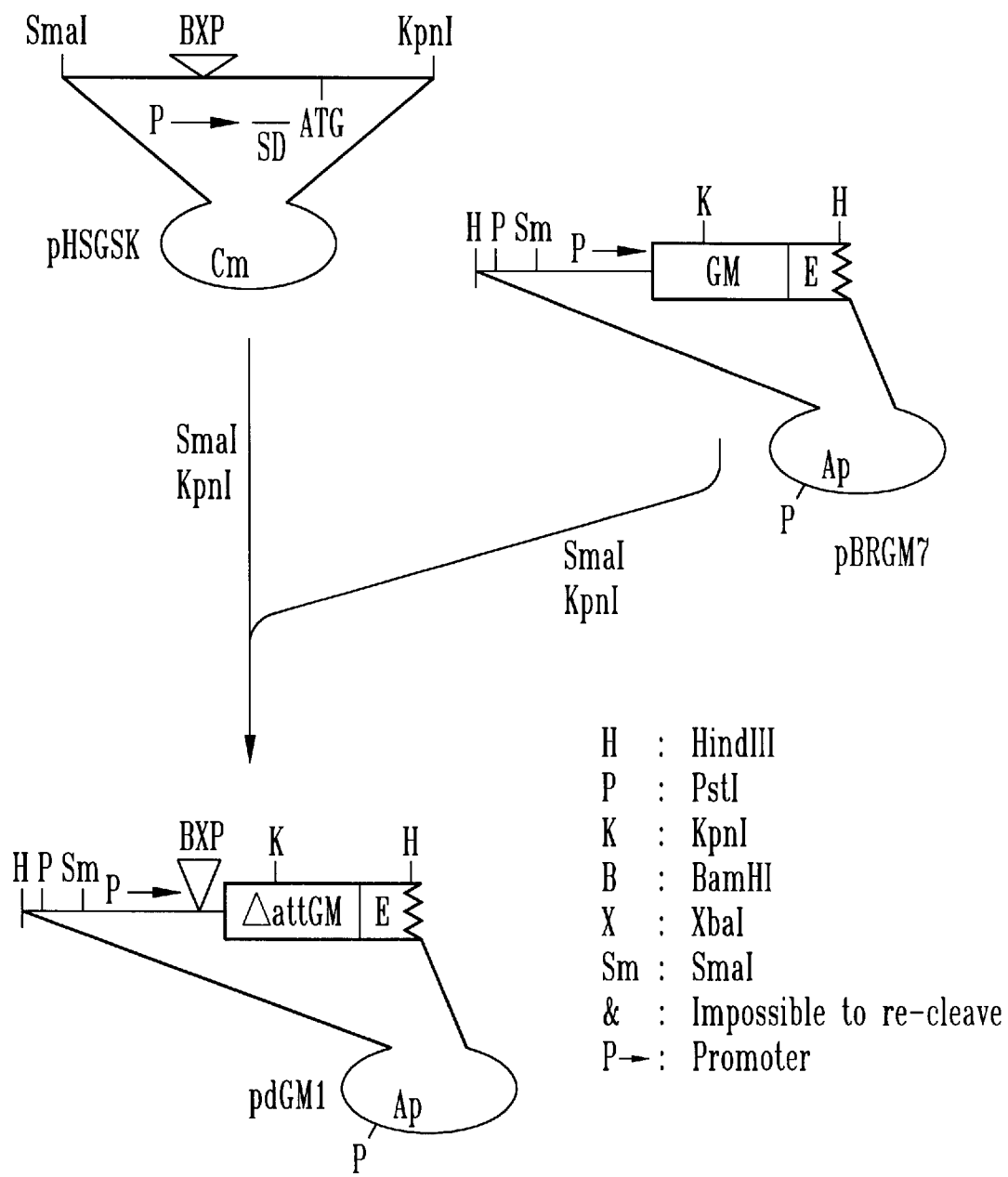
FIG. 2 is a scheme of the construction of the plasmid pdGM1.

Fragment (C) was obtained by digestion of the plasmid pHSGSK with SmaI and KpnI, the large DNA fragment was obtained by digestion of the plasmid pBRGM7 with SmaI and KpnI, and the both two fragments were ligated. The obtained plasmid was termed pdGM1. pdGM1 harbored a 4.6-kb HindIII—HindIII fragment including the ilvGM gene, which lost the region necessary for attenuation. This ilvGM gene which loses the region necessary for attenuation represents "ΔattGM". The scheme of the construction of pdGM1 is summarized in FIG. 2.

The plasmid pDRIA4 described in Japanese Patent Application Laid-Open No. 2-458(1990) is prepared by combining the shuttle vector pDR1120, which allows autonomous replication in both a microorganism belonging to the genus Escherichia and a microorganism belonging to the genus Brevibacterium, with a BamHi—BamHi fragment including the ilvA gene encoding threonine deaminase and a portion of the 3'-terminal of the ilvD gene derived from *E. coli* K-12. Japanese Patent Application Laid-Open No. 2-458(1990) describes that the length of the BamHI—BamHI fragment is 2.3 kb; however, at present, the length of this fragment has been found to be 2.75 kb. The plasmid pDRIA4 is not present within the chromosomal DNA of *Brevibacterium flavum* AJ12358 (FERM P-9764) or *Brevibacterium flavum* AJ12359 (FERM P-9765). From these strains, the plasmid pDRIA4 can be prepared according to the usual method. The feedback inhibition of threonine deaminase encoded by the ilvA gene in pDRIA4 by L-isoleucine is released, whereas this release of the feedback inhibition is not essential in the present invention.

From a 2.75-kb BamHI—BamHI DNA fragment in the plasmid pDRIA4, a HindIII-BamHI fragment including the ilvA gene encoding threonine deaminase, in which the inhibition by L-isoleucine was released, was prepared, and ligated to a DNA fragment obtained by cleaving the vector pMW119 (NIPPON GENE) with HindIII and BamHI. The resulting plasmid was termed pMWA1.

Figure 3:
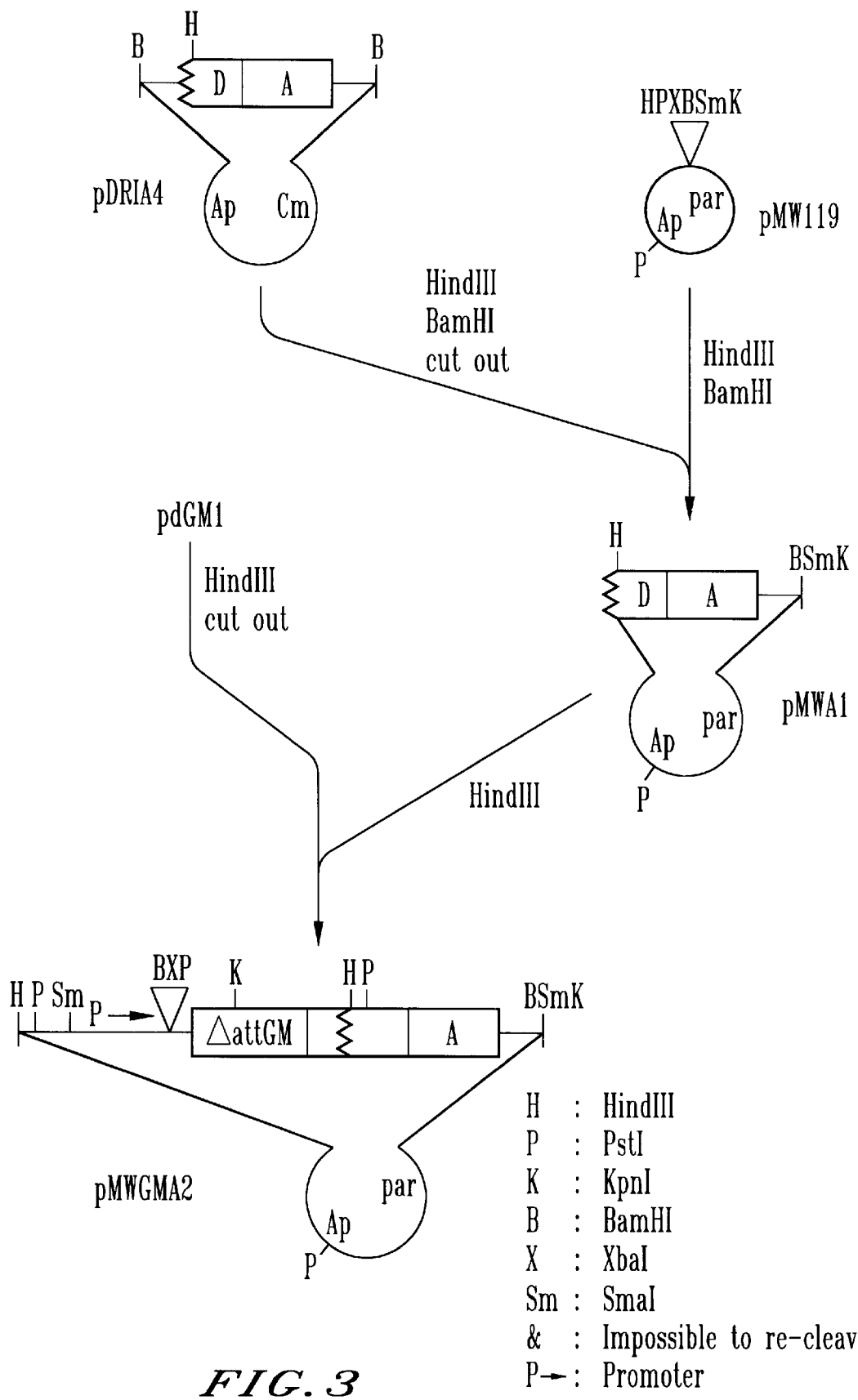
FIG. 3 is a scheme of the construction of the plasmid pMWGMA2.

A DNA fragment obtained by cleaving the plasmid pMWA1 with HindIII and a DNA fragment obtained by cleaving the plasmid pdGM1 with HindIII were ligated. According to the analysis of the position of the restriction sites of the ligated plasmids, the plasmid in which the transcriptional orientations of the ilvGM and ilvA genes were the same was selected, and termed pMWGMA2. The pMWGMA2 includes the ilvGM gene in which an attenuator was deleted, a 5'-terminal portion of the ilvE gene, and a 3'-terminal portion of the ilvD gene. The scheme of the construction of pMWGMA2 is summarized in FIG. 3.

The chromosomal DNA of *Escherichia coli* MI162 was prepared and cleaved with SalI and PstI to prepare the mixture of DNA fragments. On the other hand, a DNA fragment was prepared by cleaving the vector pUC19 (Takara Shuzo, Co., Ltd.) with SalI and PstI. The mixture of DNA fragments was ligated to the DNA fragment obtained by cleaving pUC19, and the DNA mixture was obtained. The DNA mixture was induced into AB2070, a transaminase B-deficient strain, (provided from *Escherichia coli* Genetics Stock Center. J. Bacteriol., 109, 703, (1972), CGSC2070) and a transformant, in which the branched-chain amino-acid requirement was recovered, was selected. As a result of the preparation of a plasmid from the strain, the plasmid harbored a DNA fragment obtained by cleaving the plasmid pUC19 with SalI and PstI, and a SalI-PstI DNA fragment including the ilvE gene, which were ligated. The plasmid was termed pUCE1. The pUCE1 includes a 3'-terminal portion of the ilvM gene, the ilvE gene, and a 5'-terminal portion of the ilvD gene.

Figure 4:
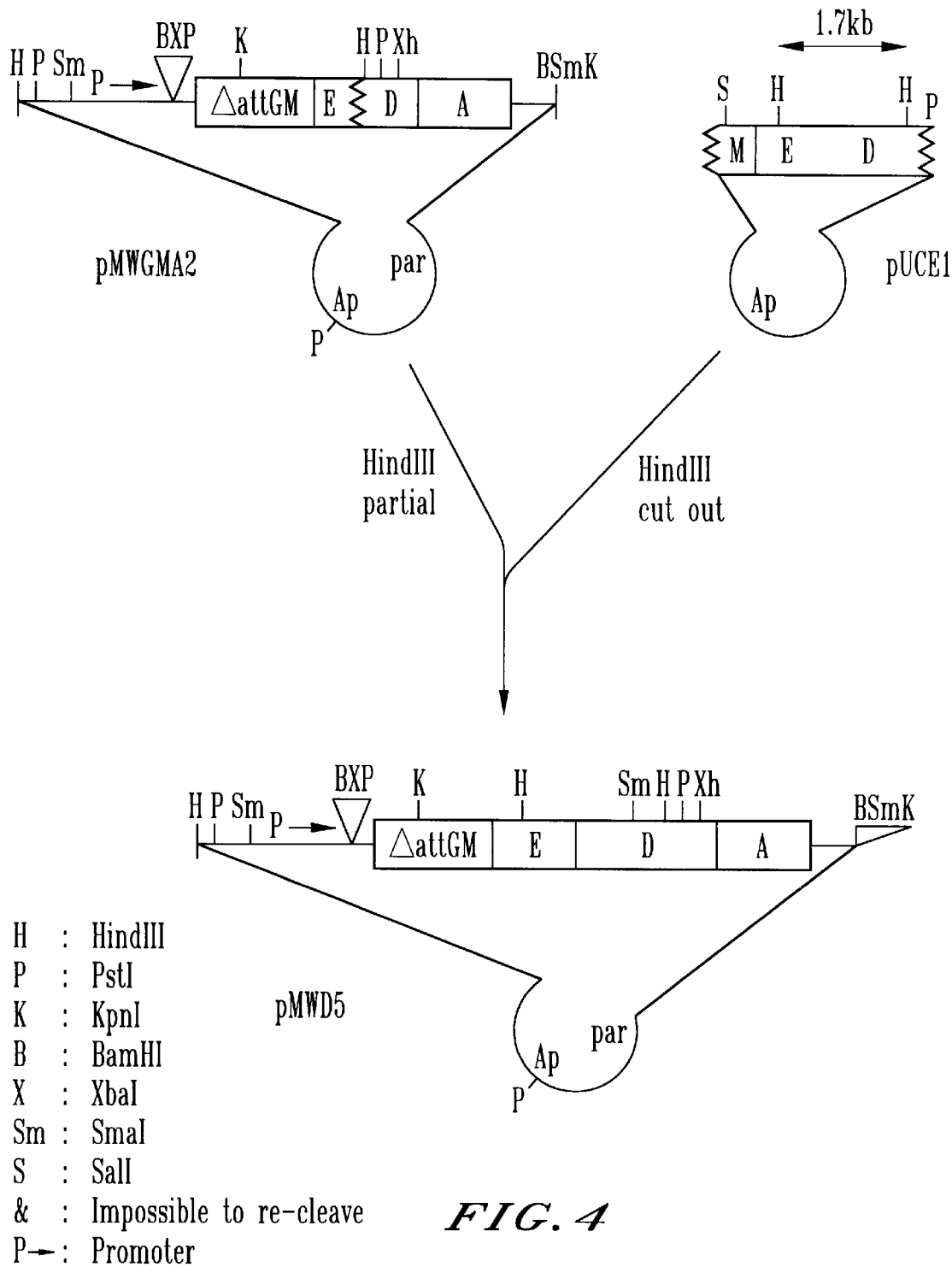
FIG. 4 is a scheme of the construction of the plasmid pMWD5.

A DNA-fragment mixture was prepared by partially digesting pMWGMA2 with HindIII. On the other hand, a 1.7-kb HindIII—HindIII DNA fragment containing a portion of the ilvE gene and a 5'-terminal portion of the ilvD gene was prepared by cleaving pUCE1 with HindIII. Using a DNA mixture obtained by ligating both of the DNA fragments, AB1280, a dihydroxy-acid dehydratase(ilvD gene product)-deficient strain, was transformed, and the strain which recovered branched chain amino acid requirement was selected from the transformants. In the plasmid prepared from the resulting transformant, a DNA fragment obtained by cleaving only the HindIII site between ΔattGM and ilvA of pMWGMA2 with HindIII, and a 1.7-kb HindIII—HindIII DNA fragment including a portion of the ilvE gene and a portion of the ilvD gene derived from pUCE1 were ligated, and the ilvGMEDA operon was reconstructed. The plasmid was termed pMWD5. The scheme of the construction of pMWD5 is summarized in FIG. 4.

The resulting plasmid pMWD5 derived from the vector pMW119 harbors the ilvGMEDA operon in which the region necessary for attenuation is deleted.

Figure 5:
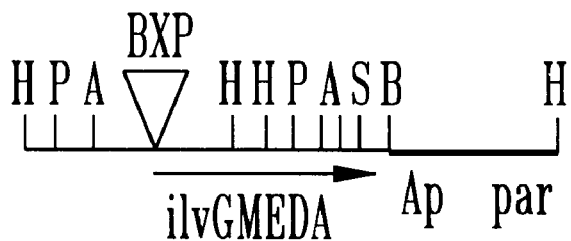
FIG. 5 is a scheme of the construction of the plasmid pMWdAR6.
Figure 5:
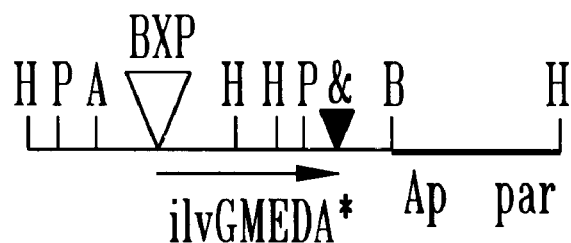

Subsequently, the plasmid pMWD5 was completely digested with SnaBI and then partially digested with AccIII. The resulting DNA fragment was self-ligated to obtain the plasmid pMWdAR6 in which only the ilvA gene was destroyed (FIG. 5). This plasmid pMWdAR6 includes the ilvGMEDA operon in which the region necessary for attenuation is deleted and the ilvA gene is destroyed.

<2> Creation of L-valine-producing-microorganism

Using the plasmid pMWdAR6 carrying the ilvGMED operon which was obtained as described above, *E. coli*

W1485lip2 (ATCC25645), a lipoic acid-requiring mutant; *E. coli* W1485atpA401, a H$^+$-ATPase-deficient mutant; *E. coli* AJ12631 (FERM P-12381); a lipoic acid-requiring and H$^+$-ATPase-deficient mutant, and wild-type *E. coli* W1485 (ATCC12435) were each transformed and the following transformants were obtained:

1) *E. coli* W1485/pMWdAR6
2) *E. coli* W1485atpA401/pMWdAR6
3) *E. coli* W1485lip2/pMWdAR6
4) *E. coli* AJ12631/pMWdAR6

*E. coli* AJ12631 was obtained by transducing atpA401, a mutant gene, encoding mutant alpha subunit of F1 of H$^+$-ATPase derived from *E. coli* AN718 (CGSC6308) into *E. coli* W1485lip2 (ATCC25645) (see Japanese Patent Application Laid-Open No. 5-137568(1993)). In selection of a transduced strain with a H$^+$-ATPase-deficient mutation, bgl gene positioned in the vicinity of atpA401 gene was used as a marker. Since the bgl gene encodes phospho-beta-glucosidase, *E. coli* having the wild-type bgl gene (bgl$^-$) cannot assimilate salicin, whereas *E. coli* having the mutant bgl gene (bgl$^+$) can grow utilizing salicin as the sole carbon source, so that the colonies of a salicin-assimilating strain make a bromothymol blue-added medium plate turn yellow by an organic acid produced by the strain. Therefore, if the mutant bgl gene (bgl$^{30}$) and atpA401 gene are linked-transduced, a H$^+$-ATPase-deficient mutant can be selected efficiently. First, the salicin-assimilating (bgl$^{30}$) strain was isolated from *E. coli* AN718, and then AN718 (bgl$^+$) was infected by P1kc, and *E. coli* W1485lip2 was transduced using the obtained lysate. For the resulting transductant, a lipoic acid requirement and H$^+$-ATPase activity was determined to confirm the presence of lipoic acid-requiring and H$^+$-ATPase-deficient mutations.

Similarly, *E. coli* W1485atpA401 was obtained by transducing atpA401 into *E. coli* W1485.

EXAMPLE 2
Production of L-valine

The L-valine productivity of L-valine-producing microorganism obtained in Example 1 was evaluated. Each of transformants was plated on the medium comprising Bacto-tryptone 1%, yeast extract 0.5%, NaCl 0.5%, agar 1.5%, and ampicillin 100 μg/ml, cultured at 37° C. for 18 to 24 hours, and then a part of them was transferred to 20 ml of a fermentation medium (glucose 4%, ammonium sulfate 1.6%, potassium dihydrogen-phosphate 0.1 , magnesium sulfate heptahydrate 0.1%, ferrous sulfate heptahydrate 0.001%, manganese sulfate pentahydrate 0.001%, yeast extract 0.2%, Bacto-tryptone 0.2%, calcium carbonate 3%, pH 7.0) with a platinum transfer loop, and incubated at 37° C. for 24 hours. In culture of lipoic acid-requiring mutant, lipoic acid was added at a final concentration of 1 μg/L.

The concentration of L-valine in the supernatant of the culture, from which the cells were removed, was determined by high-performance liquid chromatography using a cation exchange column (CPKO8: Asahi Chemical Industry Co., Ltd.). The results are shown in Table 1.

TABLE 1

| Productivity of the L-valine of each strain | |
|---|---|
| *E. coli* transformant | Productivity of L-valine (g/L) |
| W1485 | 0.1 |
| W1485/pMWdAR6 | 6.9 |
| W1485atpA401/pMWdAR6 | 8.0 |
| W1485lip2/pMWdAR6 | 7.8 |
| AJ12631/pMWdAR6 | 9.2 |

The results reveal that when a DNA fragment including the ilvDMEDA* operon in which threonine deaminase activity is not expressed and the region necessary for attenuation is deleted is introduced into a lipoic acid-requiring and/or H$^+$-ATPase-deficient *E. coli* as a host cell, the resulting *E. coli* showed enhanced productivity of L-valine. If a lipoic acid-requiring and H$^-$-ATPase-deficient strain is used as a host, the productivity of L-valine can be further enhanced.

Industrial Applicability

According to the present invention, it becomes possible to enhance the capability of L-valine or L-leucine production of a L-valine or L-leucine-producing microorganism. By using a microorganism of the present invention, L-valine and L-leucine can be produced efficiently.

---

What is claimed is:

1. A microorganism belonging to the genus Escherichia and having a capability of producing L-valine or L-leucine, which requires lipoic acid for growth, and carries a gene for L-valine or L-leucine biosynthesis, wherein the gene for L-valine or L-leucine biosynthesis carries a mutation which causes the regulator mechanism of the gene to be substantially released.

2. A microorganism according to claim 1, which has the capability of producing L-valine and carries said gene for L-valine biosynthesis.

3. A microorganism according to claim 1, which has the capability of producing L-leucine and carries said gene for L-leucine biosynthesis.

4. A microorganism according to claim 1, which is *Escherichia coli*.

5. A method for producing L-valine which comprises culturing the microorganism having the capability of producing L-valine as defined in claim 1 in a liquid medium to allow L-valine to be produced and accumulated in the medium, and collecting it.

6. A method for producing L-leucine which comprises culturing the microorganism having the capability of producing L-leucine as defined in claim 1 in a liquid medium to allow L-leucine to be produced and accumulated in the medium, and collecting it.

* * * * *